United States Patent
Bagambisa et al.

(10) Patent No.: US 8,262,389 B2
(45) Date of Patent: Sep. 11, 2012

(54) APPARATUS FOR EXPLANTING A DENTAL IMPLANT FROM A HUMAN OR ANIMAL BONE

(76) Inventors: Frank Bagambisa, Bonn (DE); Julienne Nyiramutunzi, Wachberg-Villip (DE)

( * ) Notice: Subject to any disclaimer, the term of this patent is extended or adjusted under 35 U.S.C. 154(b) by 109 days.

(21) Appl. No.: 12/565,539

(22) Filed: Sep. 23, 2009

(65) Prior Publication Data
US 2010/0081107 A1    Apr. 1, 2010

(30) Foreign Application Priority Data
Sep. 25, 2008  (DE) .......................... 10 2008 049 012

(51) Int. Cl.
*A61C 8/00* (2006.01)
(52) U.S. Cl. ................ 433/75; 606/80; 606/99
(58) Field of Classification Search ............ 433/75, 433/165, 173, 174, 176; 606/80, 96, 99
See application file for complete search history.

(56) References Cited

U.S. PATENT DOCUMENTS

| | | | | |
|---|---|---|---|---|
| 5,868,572 A | * | 2/1999 | Lazzara et al. | 433/173 |
| 5,951,286 A | * | 9/1999 | Rhodes | 433/165 |
| 6,280,197 B1 | * | 8/2001 | Benado | 433/224 |
| 7,179,084 B1 | * | 2/2007 | Kometas | 433/75 |

* cited by examiner

*Primary Examiner* — Ralph Lewis
(74) *Attorney, Agent, or Firm* — Hanley, Flight & Zimmerman, LLC

(57) ABSTRACT

The subject matter of the invention is an apparatus for explanting a dental implant from a human or animal bone. In one example, the invention may use a trephine bur on the end side of which there is formed a bur bit. In one or more examples, an apparatus by which dental implants can be drilled out accurately is achieved by a guide pin that can be attached to the dental implant and by a guide element attached to the trephine bur, said guide element cooperating with the guide pin so that the trephine bur is guided in the axial direction of the guide pin.

16 Claims, 12 Drawing Sheets

APPARATUS FOR EXPLANTING A DENTAL IMPLANT FROM A HUMAN OR ANIMAL BONE

TECHNICAL FIELD

The present invention relates to dental implants and, more particularly, to apparatus for explanting a dental implant from a human or animal bone.

BACKGROUND

To replace missing teeth, it belongs to prior art to implant into the jaw bone artificial dental implants made from titanium, ceramics or from another suited material. Sometimes however it is also necessary to remove again an existing dental implant such as when there is an inflammation or sleeping implant. In this case, the dental implant can be drilled out again, using a hollow bur such as a trephine bur the inner diameter of which is only slightly larger than the largest outer diameter of the dental implant. Then, this trephine bur is at first held onto the dental implant, relying on the visual judgment of the doctor, in such a manner that the trephine bur forms a surrounding grip, at least rudimentarily, around the upper part of the dental implant. During drilling, the trephine bur is then guided by the dental implant. However, sometimes, the drilling occurs slantwise so that, in some cases, the dental implant is even cut into pieces, which involves a complicated surgical intervention in order to remove the rests of the dental implant.

DETAILED DESCRIPTION

Figure 1:
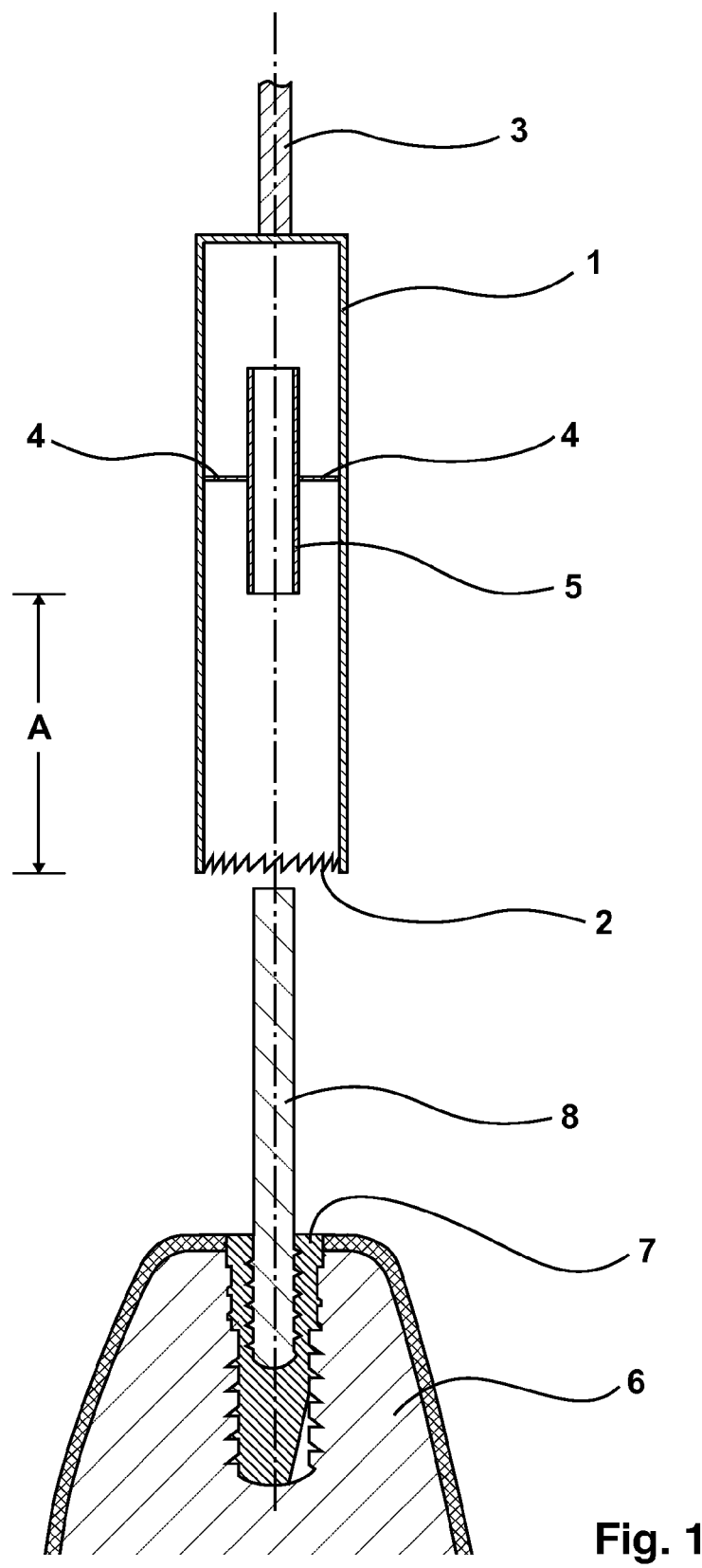
FIG. 1 is a side sectional view of a first example of an apparatus in accordance with the teachings of the present invention together with a sectional view of a dental implant in a jaw bone prior to drilling.

In the FIGS. 1 through 4 there is shown a first example apparatus in accordance with the teachings of the present invention at different instants in time. This example apparatus incorporates a hollow cylindrical trephine bur 1 on the end side of which there is formed a bur bit 2. Opposite the bur bit 2 a bur receiving mount 3 is attached to the trephine bur 1, said bur receiving mount serving to couple the trephine bur 1 to a corresponding drive which has not been illustrated in closer detail herein. In the interior of the trephine bur 1 a guide element 5 is retained through four webs 4. This guide element 5 is configured to be hollow cylindrical and is disposed coaxially with respect to the trephine bur 1.

A dental implant 7 is implanted in the jaw bone 6 and a guide pin 8 is placed in this dental implant 7. The guide pin 8 is disposed coaxial with the dental implant 7, i.e., the virtual longitudinal axis of the guide pin 8 and the virtual longitudinal axis of the dental implant 7 are identical or substantially identical.

In one example, the distance A between the end side of the trephine bur 1 and the lower end side of the guide element 5 is at least equal to the length of the dental implant 7 whilst the guide pin 8 is considerably longer than the distance A so that the guide pin 8 already extends into the guide element 5 whilst the trephine bur 1 still fits against the jaw bone 6.

In another example that has not been illustrated herein, the distance A substantially corresponds to the length of the dental implant 7.

One example way in which such a drilling operation is performed will be described in detail herein after.

Figure 2:
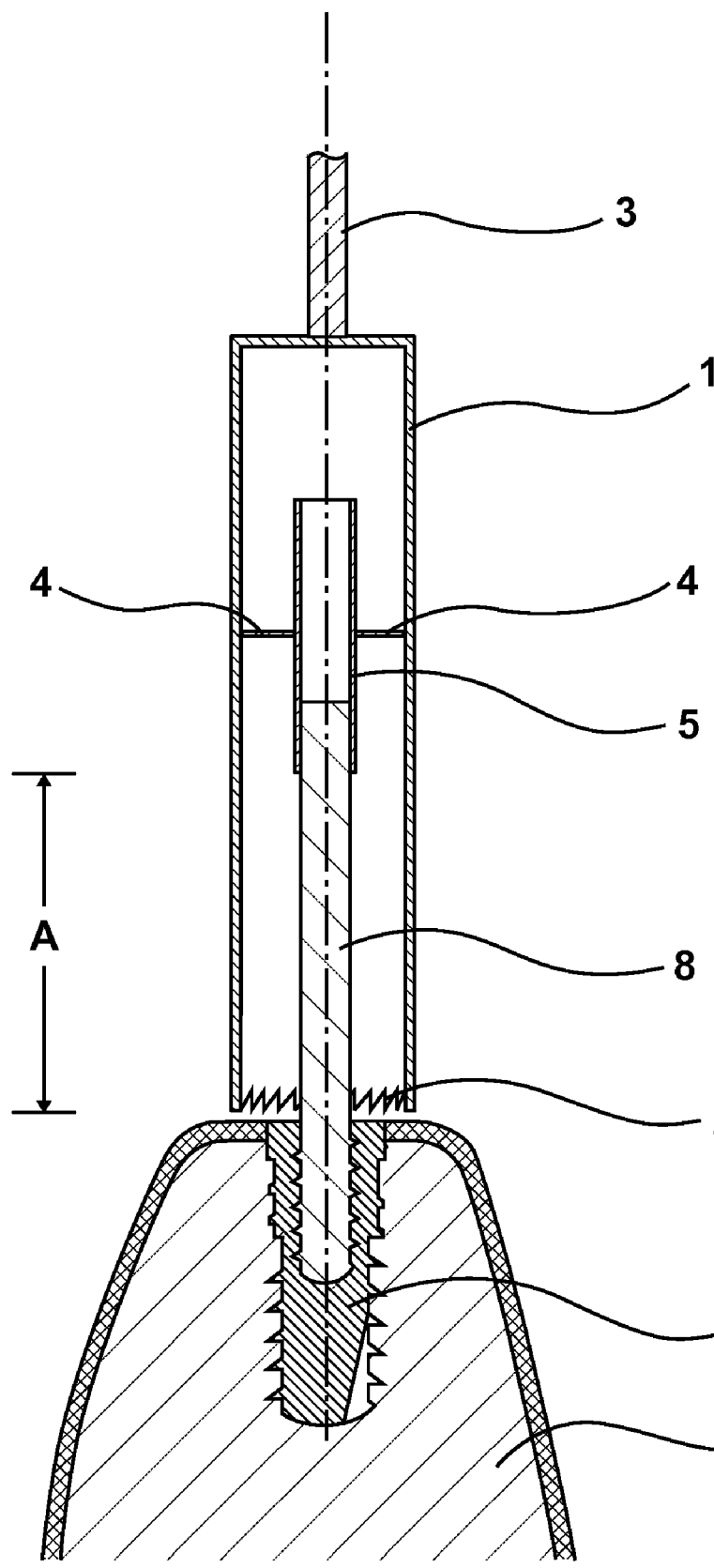
FIG. 2 shows the apparatus shown in FIG. 1 directly before penetration of the trephine bur into the jaw bone.
Figure 3:
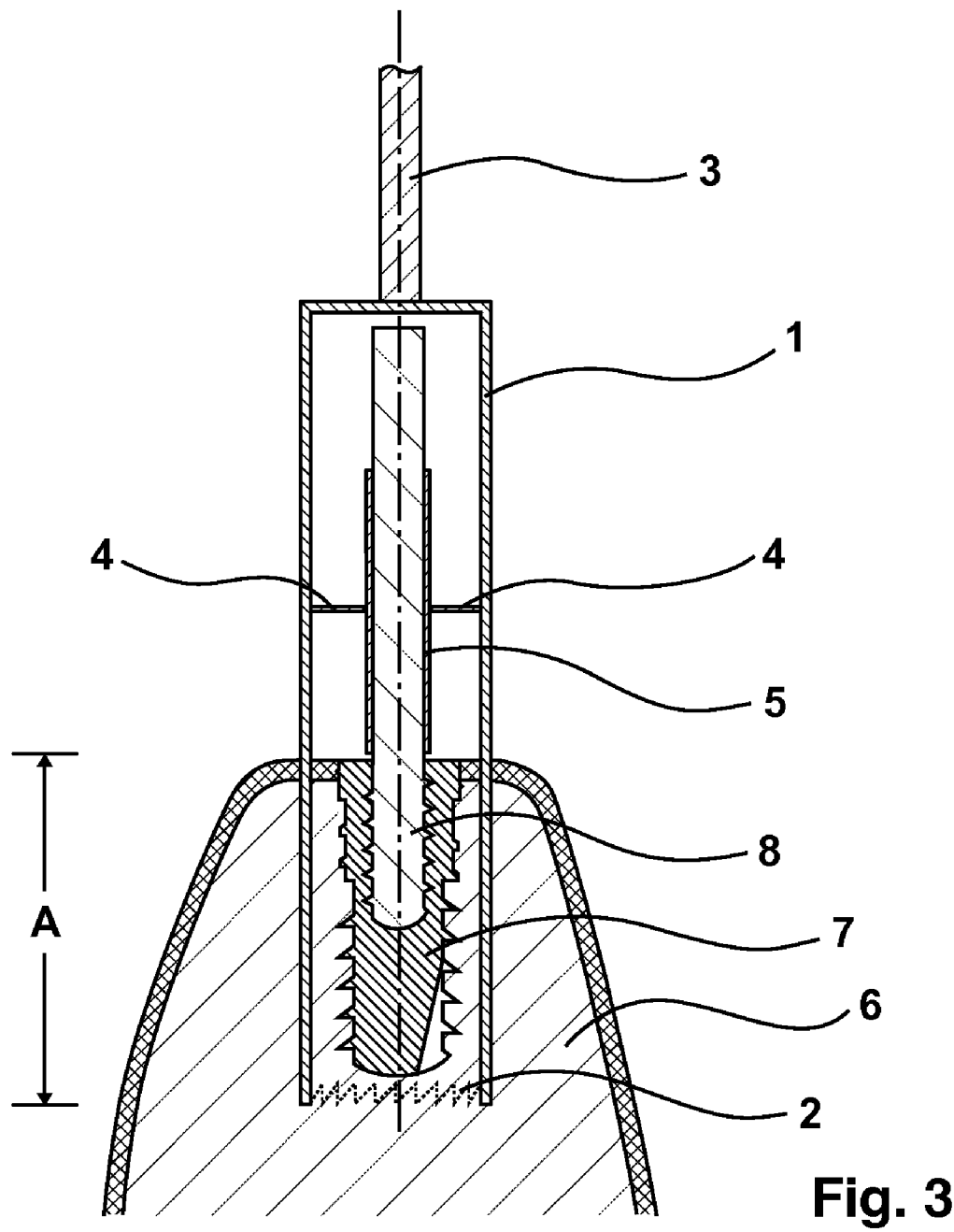
FIG. 3 shows the apparatus shown in FIG. 1 upon completion of the drilling operation.
Figure 4:
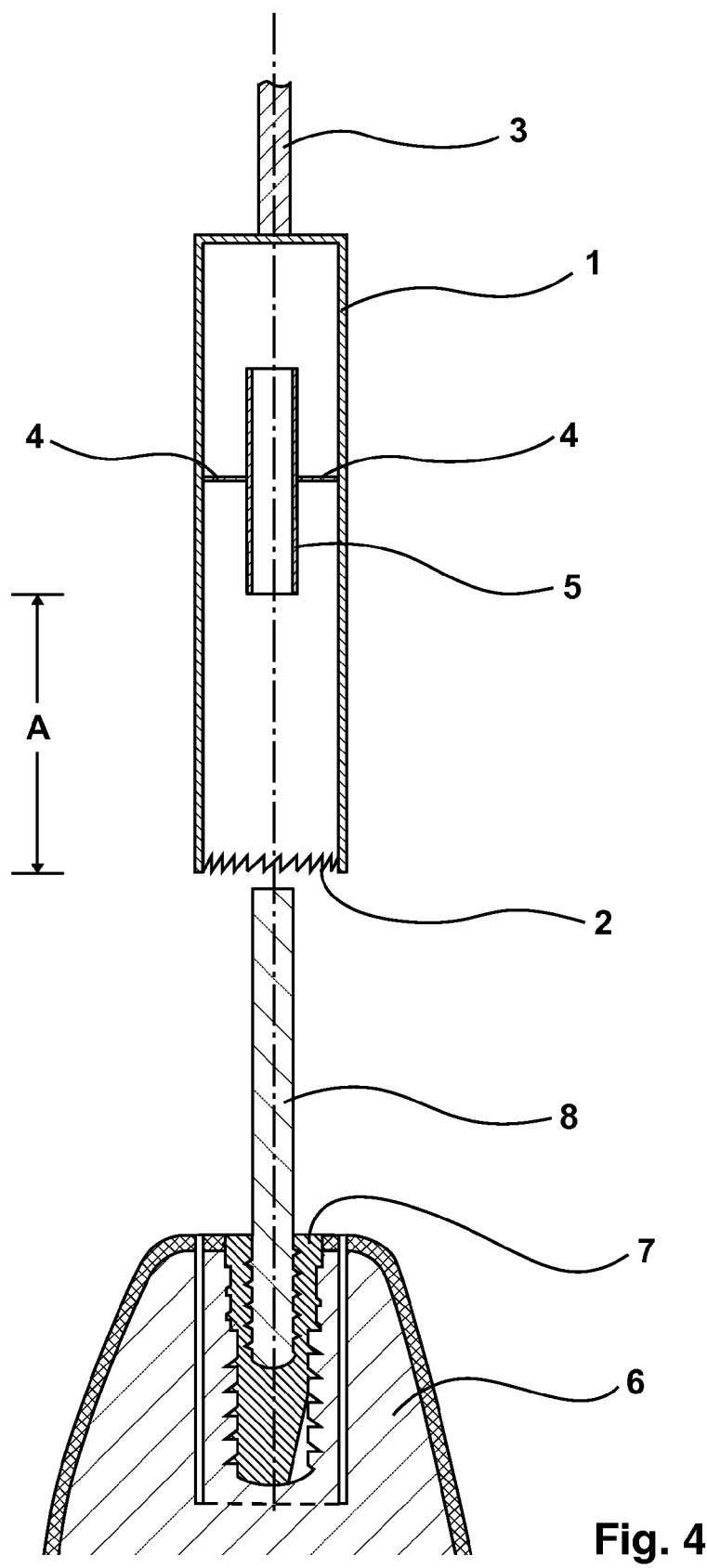
FIG. 4 shows the apparatus shown in FIG. 1 with the trephine bur removed.
Figure 5:
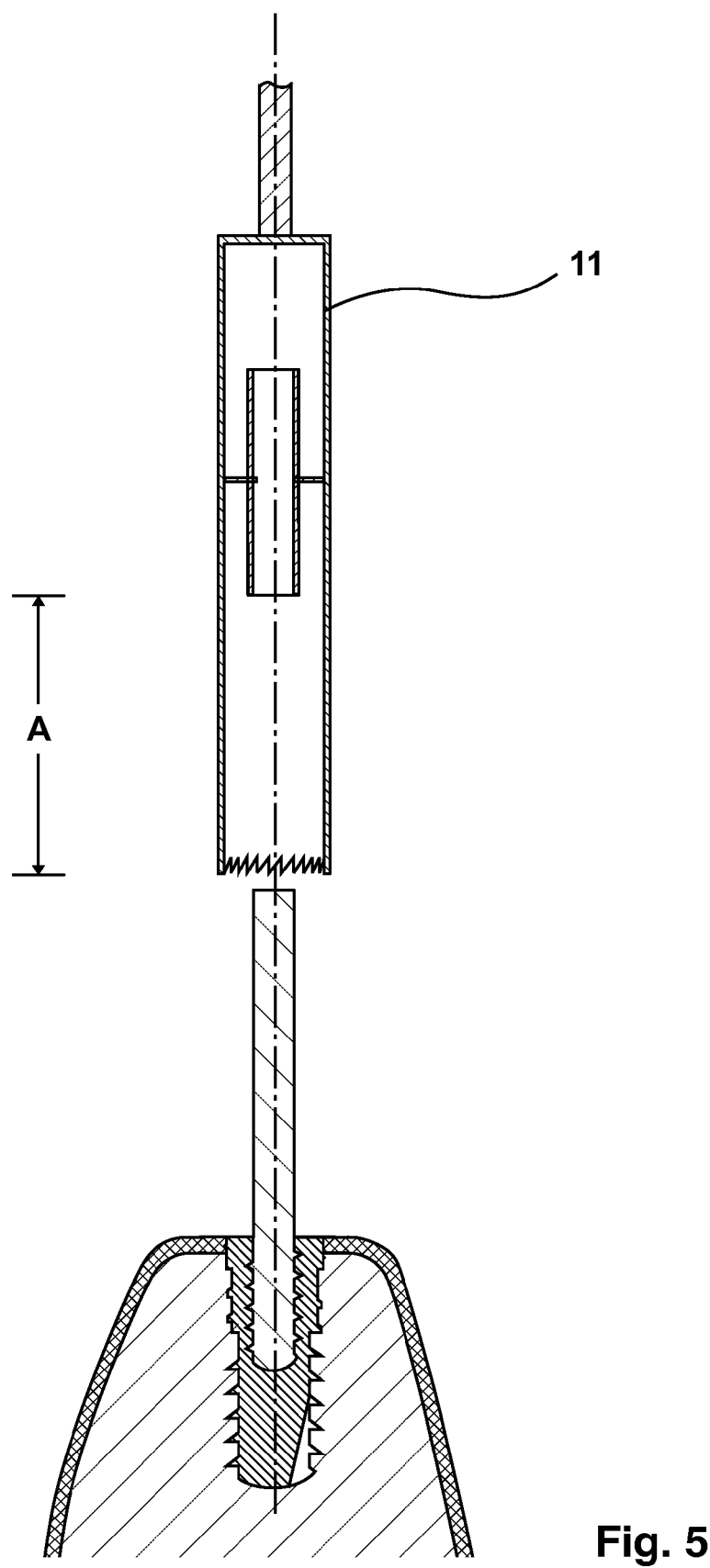
FIG. 5 shows a sectional side view of a second example of an apparatus in accordance with the teachings of the present invention together with a sectional view of a dental implant in a jaw bone before beginning with the drilling operation.
Figure 6:
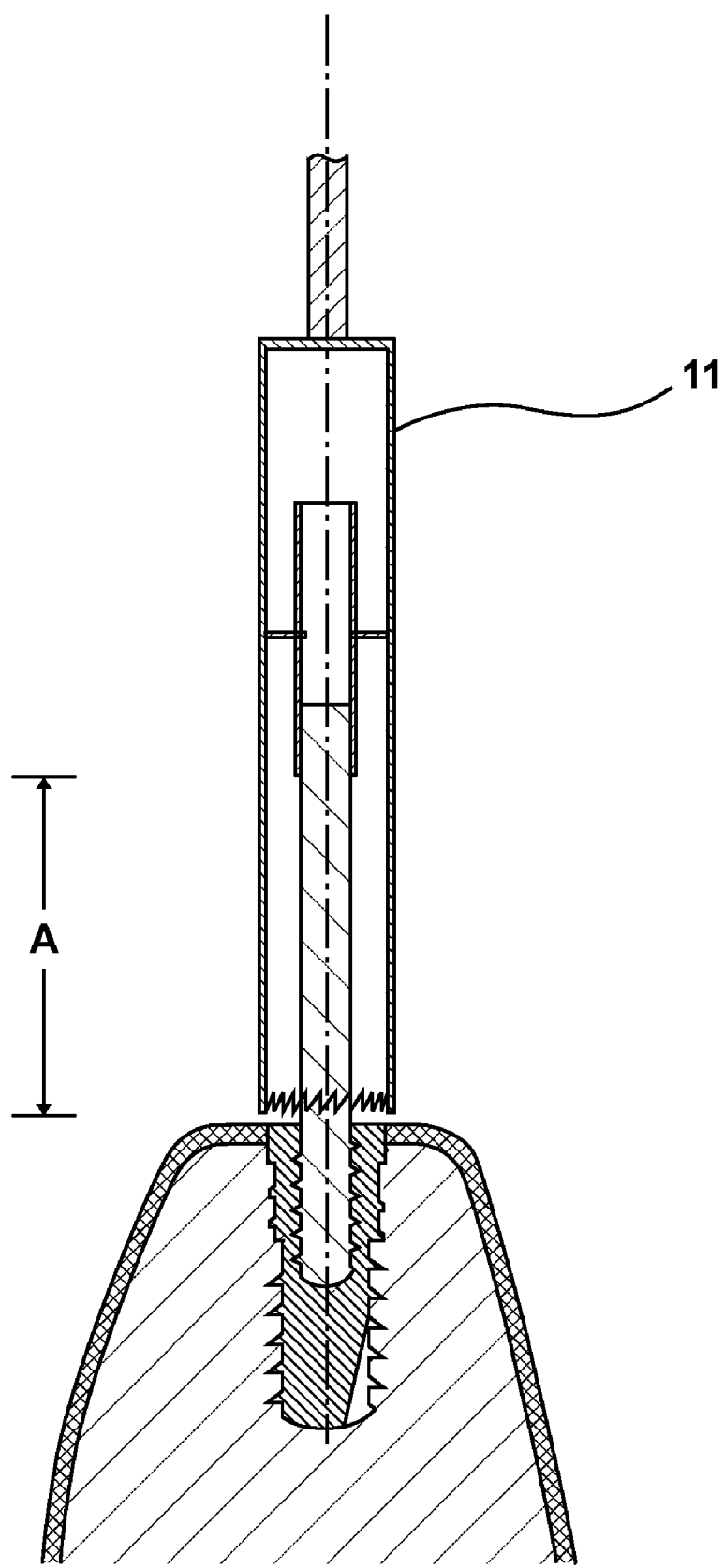
FIG. 6 shows the apparatus shown in FIG. 5 directly before penetration of the trephine bur into the jaw bone.
Figure 7:
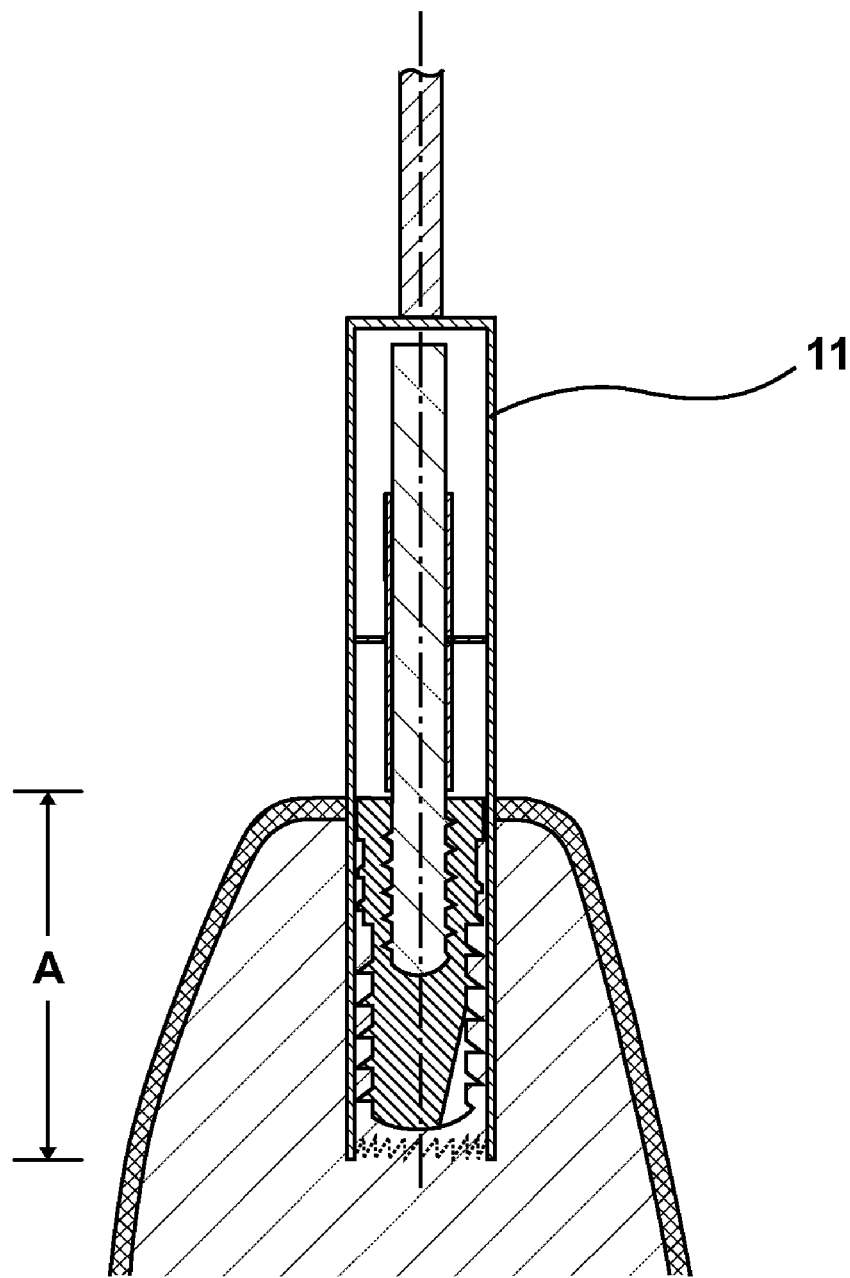
FIG. 7 shows the apparatus shown in FIG. 5 upon completion of the drilling operation.
Figure 8:
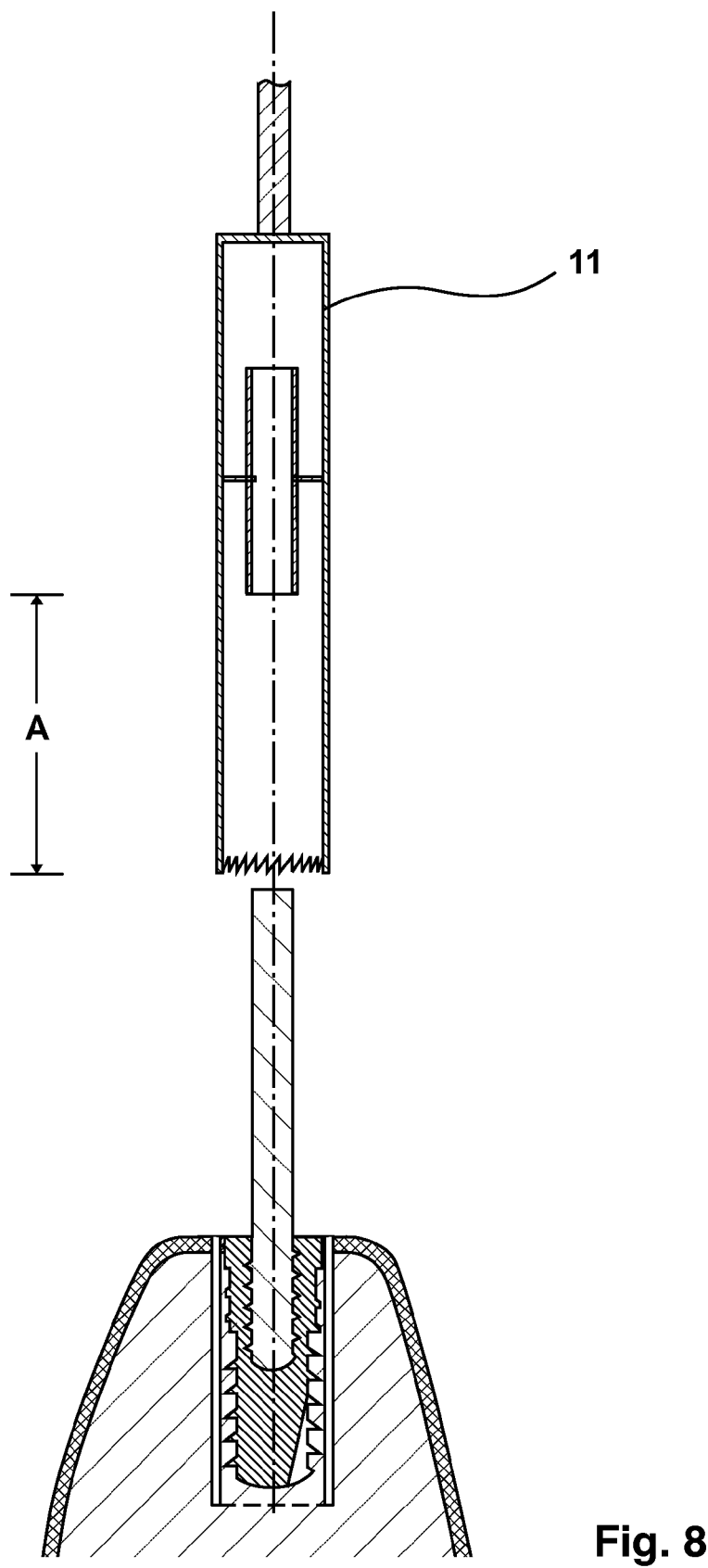
FIG. 8 shows the apparatus shown in FIG. 5 with the trephine bur removed.

At first, the guide pin 8 is placed into the dental implant 7 (FIG. 1) so that the guide pin 8 is disposed coaxial, or substantially coaxial, with the dental implant 7. Then, the trephine bur 1, with the guide element 5 disposed coaxially therein, is guided over the guide pin 8 so that the guide pin 8 enters into the interior of the guide element 5 (FIG. 2). Thanks to the cooperation between guide pin 8 and guide element 5, the trephine drill 1 is oriented coaxial with the dental implant 7. If drilling is now performed, the trephine bur 1 is reliably guided coaxial with the dental implant 7 thanks to the cooperation between guide pin 8 and guide element 5 (FIG. 3). Upon completion of the drilling operation, the trephine bur 1 is removed from the jaw bone 6. At last, the dental implant 7 is removed, the bone on the end side of the dental implant 7 having to be detached first. In the first example shown in the FIGS. 1 through 4, the clear diameter of the bur 1 is approximately 1 millimeters (mm) to 6 mm, in one example preferably 3 mm larger than the largest outer diameter of the dental implant 7. As a result, the dental implant 7 can be removed together with the bone substance 6 surrounding the implant. Such a dental implant 7 can then be implanted somewhere else, for example at a place with but little bone substance.

The second example shown in the FIGS. 5 through 8 differs from the first example by the fact that here the diameter of the trephine bur 11 is but slightly larger than the largest outer diameter of the dental implant. As a result, the dental implant can be drilled out accurately, meaning with a minimum of bone matter. Such a trephine bur 11 is typically chosen when the implant is not intended for further use.

Figures 9, 9A, 9B:
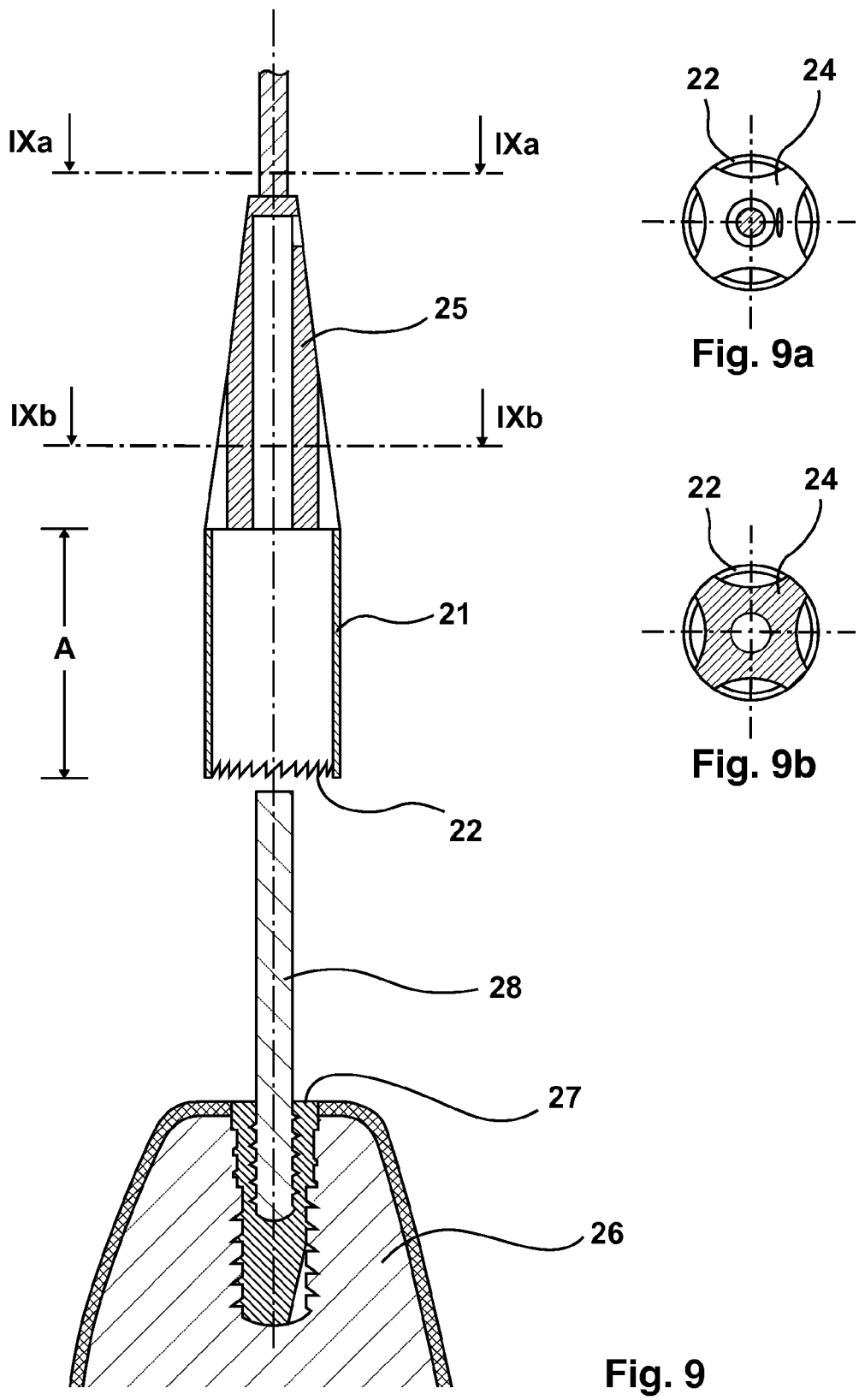
FIG. 9 shows a sectional side view of a third example of an apparatus in accordance with the teachings of the present invention together with a sectional view of a dental implant in a jaw bone prior to drilling.
FIG. 9a shows a sectional top view of the apparatus shown in FIG. 9, taken along section line IXa to IXa in FIG. 9.
FIG. 9b shows a sectional top view of the apparatus shown in FIG. 9, taken along section line IXb bis IXb in FIG. 9.
Figure 10:
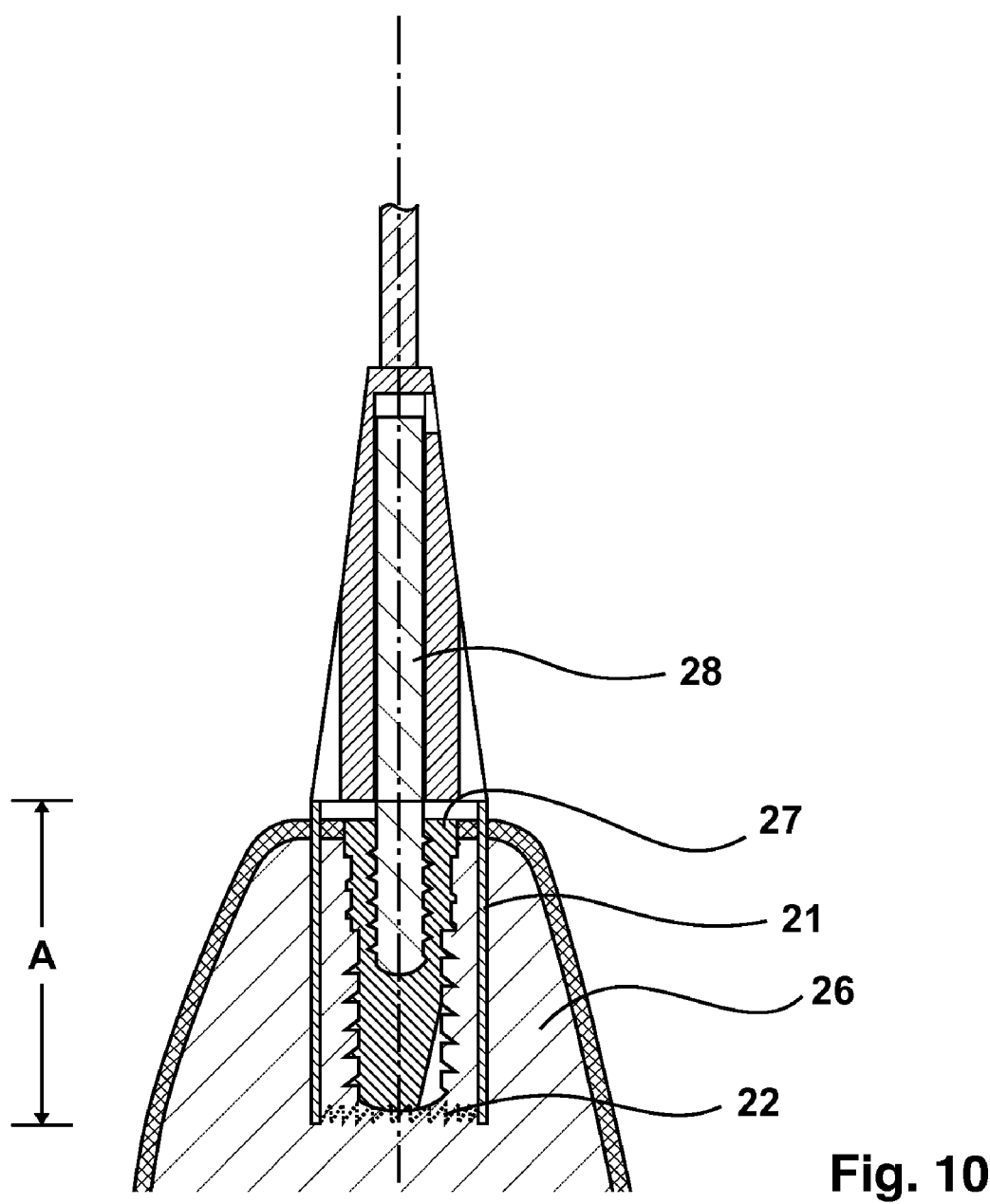
FIG. 10 shows the apparatus shown in FIG. 9 upon completion of the drilling operation.

In the FIGS. 9 through 10, there is shown a third example. According to the third example, an implant 27 is embedded in a jaw bone 26, a guide pin 28 being placed into the implant 27. Above the trephine bur 21 there is mounted a hollow cylindrical guide element 25 which is retained on the trephine bur 21 through four webs 24. This trephine bur 21 also has a bur bit 22 on its end side.

Unlike the first example shown in the FIGS. 1 through 4, the guide element 25 is here disposed outside of the trephine bur 21, but is also configured to be hollow cylindrical for reception of the guide pin 28. For the rest of the description, this third example substantially corresponds to the first example, which is shown in the FIGS. 1 through 4.

Figure 11:
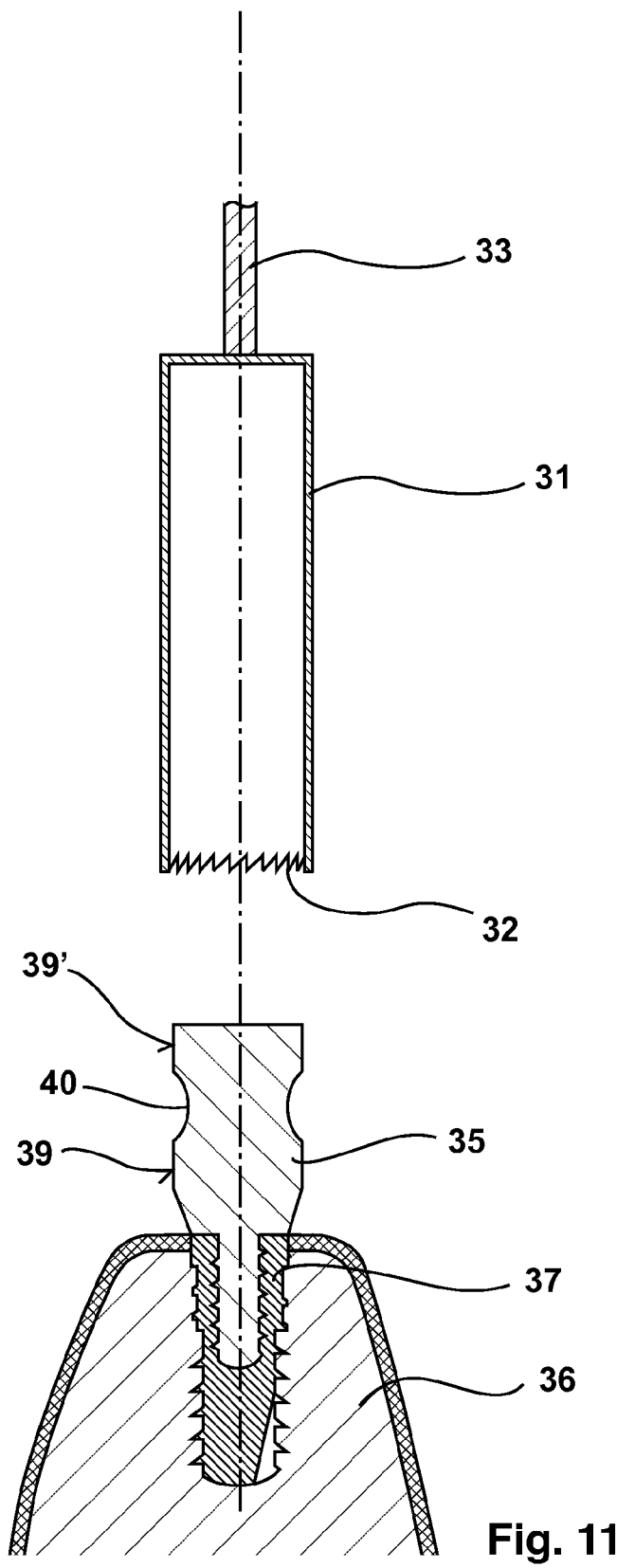
FIG. 11 shows a sectional side view of a fourth example of an apparatus in accordance with the teachings of the present invention together with a sectional view of a dental implant in a jaw bone before beginning with the drilling operation.
Figure 11A:
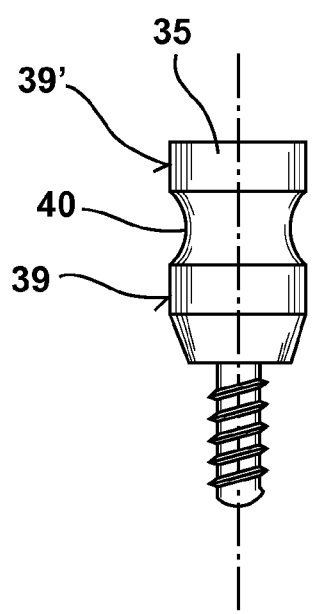
FIG. 11a is a side view of the guide cylinder of the apparatus shown in FIG. 11.
Figure 12:
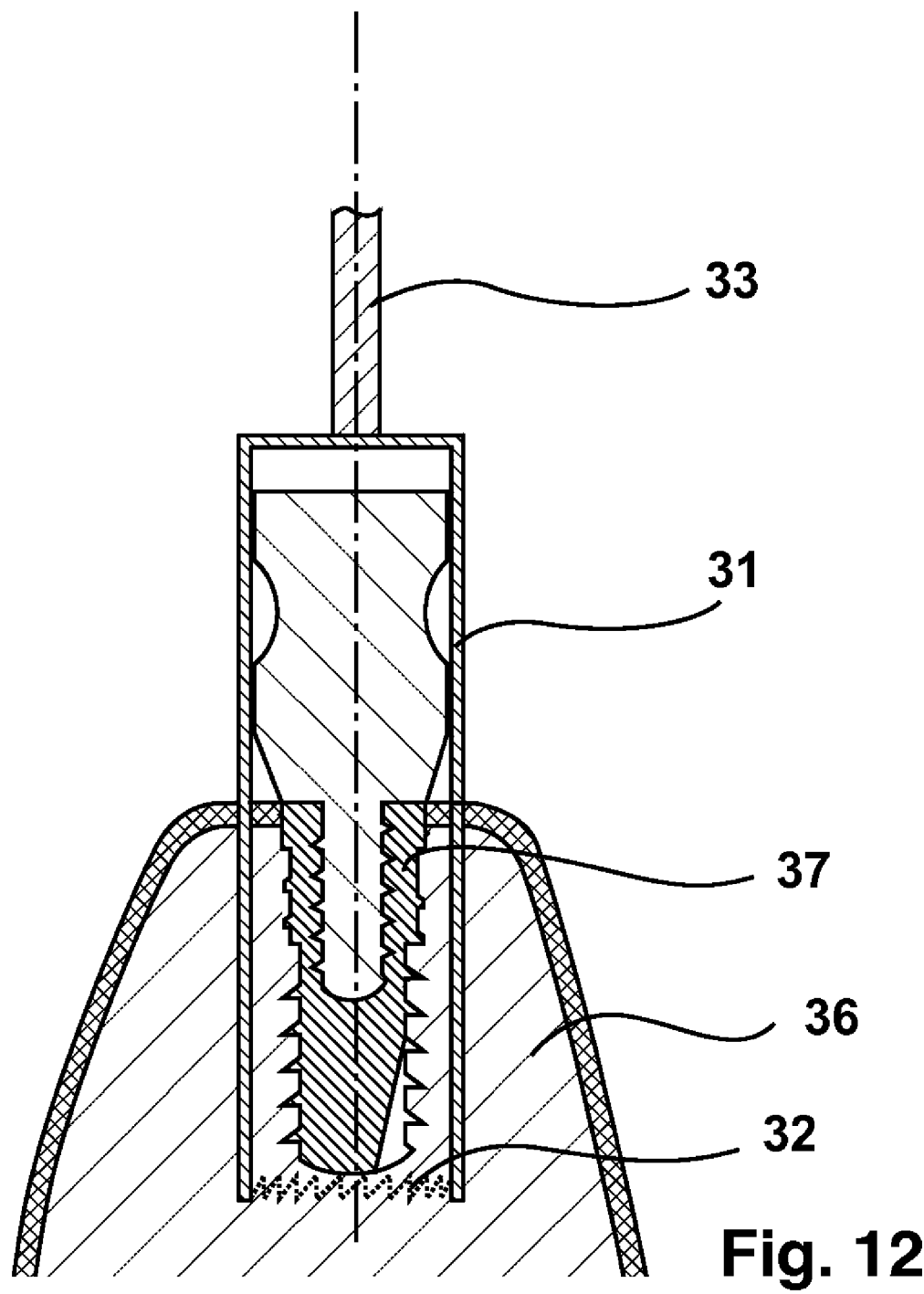
FIG. 12 shows the apparatus shown in FIG. 11 upon completion of the drilling operation.

In the fourth example shown in the FIGS. 11 through 12, and unlike in the first three examples, a commercially available trephine bur 32 is used, which is driven through a bur reception mount 33 and also has a bur bit 32. In this example, a guide cylinder 35, which can be placed into the implant 37, is utilized instead of the guide pin. This guide cylinder 35 can be fixed in the implant 37 through a receiving portion, here a thread.

Above the implant 37, two guide surfaces 39 and 39' are configured on the guide cylinder 35. In the region of these guide surfaces 39 and 39', the guide cylinder 35 is configured to be cylindrical whilst the guide cylinder 35 comprises, in the region between the guide surfaces 39 and 39', a groove 40 so that the guide surfaces 39 and 39' are spaced apart by said groove 40. In the region of the guide surfaces 39 and 39', the outer diameter of the guide element 35 substantially corresponds to the clear inner diameter of the trephine bur 31 so that the guide cylinder 35 can be introduced into the trephine bur 31, guiding said bur coaxial with the implant 37 during the drilling operation.

If the physician uses a trephine bur and a guide cylinder the diameters of which correspond to the diameter of the implant, the implant is drilled out without bone substance. If, by contrast, it uses a trephine bur and a guide cylinder whose diameter is larger than the implant, bone substance is drilled out, together with the implant, and said bone substance can be implanted again somewhere else.

Each implant manufacturer gives the receptacle for its implant an individual shape. It may be, as shown herein, a thread, but it may also be of another shape. It is understood that the fastening means of the guide pin or of the guide cylinder is configured according to the receptacle of the implant and needs not be a thread like in these examples.

In another example that has not been illustrated herein, the trephine drill may be equipped with an ultrasonic cutting apparatus or with a piezo cutting apparatus.

In view of the foregoing, the examples described herein may provide an apparatus of the type mentioned herein above by means of which dental implants can be drilled out in an axially parallel manner. The inventions, as defined by the claims appended hereto, provide a technical solution to facilitate the results achieved by the examples.

One or more of the foregoing examples are advantageous in that, through the cooperation of guide pin and guide element or of guide cylinder and trephine bur, one realizes a reliable guidance of the trephine bur so that said bur can penetrate into the bone, guided so as to be coaxial with the dental implant. One thus achieves that the dental implant is not damaged and can be readily and completely removed.

Another advantage realized by one or more of the foregoing examples is that, by drilling around the implant in an axially parallel manner, one also burs out a certain amount of bone substance, the bone substance about the implant being of uniform thickness. Depending on the size of the trephine bur, the belt of bone substance around the implant can be more or less thick.

In a preferred example, the guide element is configured to be hollow cylindrical, the clear width of the guide element being chosen to correspond to the diameter of the guide pin. The advantage thereof is that the guide element attached to the trephine bur receives the guide pin attached to the dental implant in order to thus realize a reliable guidance of the trephine bur. It is understood that the clear width of the guide element is configured to be so much larger than the diameter of the guide pin that the guide pin can be introduced readily into the guide element whilst concurrently the clear width of the guide element will not be chosen to be much larger than the diameter of the guide pin so that the guide pin can be guided in the guide element with only a small clearance. This applies in analogous fashion for the guide cylinder and the trephine bur.

It has proved advantageous to, in some examples, coaxially attach the guide element to the trephine bur and to also coaxially attach the guide pin in the dental implant. One thus achieves that the trephine bur is guided coaxial with the dental implant so that the distance between the dental implant and the interior of the trephine bur is approximately equal over the circumference of the dental implant.

In a preferred example the guide element is retained on the trephine bur through three to eight, preferably through four webs. Thanks to these webs, the trephine bur is open toward the top so that material possibly needed during the intervention may be fed or other material may be evacuated as a result thereof.

In another preferred example, the guide pin already extends into the guide element when the trephine bur still fits against the bone. This offers the advantage that a guide of the trephine bur is already coaxial with the dental implant before the actual drilling begins so that it is no longer necessary to correct the orientation during the drilling operation.

In still another preferred example, the guide element is spaced a distance from the bur bit that is equal to the length of the dental implant. The advantage thereof is that the trephine bur can penetrate so far into the bone until it reaches the lower end of the dental implant so that the dental implant can be completely drilled out.

In another preferred example, the guide element is integral with the trephine bur, which contributes to simplify the manufacturing of the trephine bur.

In another, particularly preferred example, a guide cylinder is used instead of the guide pin, the outer diameter of said guide cylinder corresponding to the clear inner diameter of the trephine bur. This offers the advantage that a commercially available trephine bur can be used while still achieving a coaxial guidance of the trephine bur.

In an advantageous developed implementation, preferably two (at least one however) guide surfaces are formed on the circumference of the guide cylinder, said guide surfaces serving to bring the guide cylinder to abut in the interior of the trephine bur and to guide it. These guide surfaces are spaced apart in order to avoid canting.

This patent application makes reference to, incorporates the same herein by reference, and claims all benefits accruing under 35 U.S.C. §119 from an application for patent filed in the German Patent Office on Sep. 25, 2008, and there assigned Serial No. DE 10 2008 049 012.1.

Further advantages of the example apparatus constructed in accordance with the invention described herein will become apparent in the appended drawings and the foregoing description of examples thereof. Likewise, the invention lies in each and every novel feature or combination of features mentioned above or described herein after. The examples provided are not intended to limit the scope of the invention in any manner. Although certain example apparatus, methods, and articles of manufacture are described herein, other implementations are possible. The scope of coverage of this patent is not limited to the specific examples described herein. On the contrary, this patent covers all apparatus, methods, and articles of manufacture falling within the scope of the invention.

What is claimed is:

1. An apparatus for explanting a dental implant from a human or animal bone, the apparatus comprising:
    a trephine bur;
    a bur bit on an end of the trephine bur;
    a guide pin attachable to the dental implant; and
    a guide element attached to the trephine bur, the guide element cooperating with the guide pin to guide the trephine bur in an axial direction of the guide pin to explant the dental implant, wherein the guide element is coaxially retained inside the trephine bur and the guide pin is coaxially retained with the trephine bur in the dental implant.

2. The apparatus as set forth in claim 1, wherein the guide element is a hollow cylinder having a width substantially corresponding to a diameter of the guide pin.

3. The apparatus as set forth in claim 1 further comprising a plurality of webs to retain the guide element in the trephine bur.

4. The apparatus as set forth in claim 1, wherein the guide pin is to extend into the guide element when the trephine bur fits against a jaw bone.

5. The apparatus as set forth in claim 1, wherein a distance between the guide element and the bur bit substantially corresponds to a length of the dental implant.

6. The apparatus as set forth in claim 1, wherein a distance between the guide element and the bur bit corresponds at least to a length of the dental implant.

7. The apparatus as set forth in claim 1, wherein the guide element is integral with the trephine bur.

8. The apparatus as set forth in claim 1, wherein the guide element is to be disposed over a top of the guide pin.

9. The apparatus as set forth in claim 1, wherein the trephine bur comprises a sidewall and the position of the guide element does not change relative to the sidewall during movement of the trephine bur.

10. The apparatus of claim 1, herein the guide pin comprises an extension to penetrate the dental implant.

11. An apparatus for explanting a dental implant from a human or animal bone, the apparatus comprising:
    a trephine bur;
    a bur bit on an end of the trephine bur;
    a guide pin attachable to the dental implant; and
    a guide element attached to the trephine bur, the guide element cooperating with the guide pin to guide the trephine bur in an axial direction of the guide pin to explant the dental implant, wherein the guide element is disposed above the trephine bur.

12. An apparatus for explanting a dental implant from a human or animal bone, the apparatus comprising:
    a trephine bur;
    a bur bit on an end of the trephine bur;
    a guide pin attachable to the dental implant; and
    a guide element attached to the trephine bur, the guide element cooperating with the guide pin to guide the trephine bur in an axial direction of the guide pin to explant the dental implant, wherein the trephine bur is open at the top and the guide element is spaced from an interior wall of the trephine bur to feed material into the trephine bur or evacuate material from the trephine during the explanting of the dental implant.

13. An apparatus for explanting a dental implant from a human or animal bone, the apparatus comprising:
    a trephine bur;
    a bur bit on an end of the trephine bur;
    a guide pin attachable to the dental implant;
    a guide element attached to the trephine bur, the guide element cooperating with the guide pin to guide the trephine bur in an axial direction of the guide pin to explant the dental implant; and
    a plurality of webs to immovably couple the guide element to the trephine bur.

14. The apparatus of claim 13, wherein the plurality of webs comprises four webs.

15. The apparatus of claim 13 further comprising an open space between each of the webs.

16. The apparatus of claim 13, wherein each web is coupled to another web.

* * * * *